US012661080B2

(12) United States Patent (10) Patent No.: US 12,661,080 B2
Ono (45) Date of Patent: Jun. 23, 2026

(54) PET-CT APPARATUS, MEDICAL IMAGE PROCESSING METHOD, AND NON-TRANSITORY COMPUTER-READABLE MEDIUM

(71) Applicant: Canon Kabushiki Kaisha, Tokyo (JP)

(72) Inventor: Shogo Ono, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 50 days.

(21) Appl. No.: 18/366,231

(22) Filed: Aug. 7, 2023

(65) Prior Publication Data

US 2024/0050057 A1 Feb. 15, 2024

(30) Foreign Application Priority Data

Aug. 10, 2022 (JP) ................................. 2022-128421

(51) Int. Cl.
A61B 6/00 (2024.01)
A61B 6/03 (2006.01)
(52) U.S. Cl.
CPC ............ A61B 6/5235 (2013.01); A61B 6/032 (2013.01); A61B 6/037 (2013.01); A61B 6/5217 (2013.01)
(58) Field of Classification Search
CPC ....... A61B 6/5235; A61B 6/032; A61B 6/037; A61B 6/5217; A61B 6/5205; A61B 6/5264; A61B 6/4035; A61B 6/4417; A61B 6/5288
See application file for complete search history.

(56) References Cited

U.S. PATENT DOCUMENTS

| | | | | |
|---|---|---|---|---|
| 2011/0286574 A1* | 11/2011 | Suzuki | ................... | A61B 6/542 |
| | | | | 378/8 |
| 2012/0275657 A1* | 11/2012 | Kolthammer | .......... | A61B 6/037 |
| | | | | 382/107 |
| 2014/0205165 A1* | 7/2014 | Jeanne | ................. | G06V 10/143 |
| | | | | 382/128 |
| 2015/0206288 A1* | 7/2015 | Verma | .................. | A61B 6/5288 |
| | | | | 382/131 |
| 2021/0065412 A1* | 3/2021 | Feng | ..................... | G06T 11/005 |

FOREIGN PATENT DOCUMENTS

JP 2012-189362 A 10/2012

* cited by examiner

*Primary Examiner* — Kaitlyn E Sebastian
(74) *Attorney, Agent, or Firm* — Oblon, McClelland, Maier & Neustadt, L.L.P.

(57) ABSTRACT

A PET-CT apparatus according to the embodiment includes processing circuitry. The processing circuitry scans a subject to acquire an attenuation-correcting CT image, identifies a respiratory phase of the subject when the CT image is scanned, acquires PET scan data that is based on a gamma ray emitted from the subject, generates gate data by gating the PET scan data based on the respiratory phase, and reconstructs a PET image based on the CT image and the gate data.

7 Claims, 5 Drawing Sheets

CT RESPIRATORY
WAVEFORM

T1

AMPLITUDE

TIME

PET RESPIRATORY
WAVEFORM

T2     T3

AMPLITUDE

P2     TIME     P3

PET-CT APPARATUS, MEDICAL IMAGE PROCESSING METHOD, AND NON-TRANSITORY COMPUTER-READABLE MEDIUM

CROSS-REFERENCE TO RELATED APPLICATIONS

This application is based upon and claims the benefit of priority from Japanese Patent Application No. 2022-128421, filed on Aug. 10, 2022, the entire contents of which are incorporated herein by reference.

FIELD

An embodiment described herein relates generally to a PET-CT apparatus, a medical image processing method, and a non-transitory computer-readable medium.

BACKGROUND

Conventionally, X-ray diagnostic apparatuses such as a positron emission tomography (PET) apparatus and a computed tomography (CT) apparatus have been put in use. There are also some X-ray diagnostic apparatuses including an integration of a PET apparatus and a CT apparatus (hereinafter referred to as PET-CT apparatus). Such a PET-CT apparatus generates a PET image by applying a reconstruction process to raw PET data acquired by the PET apparatus. At this time, the PET-CT apparatus also performs correction of the raw PET data, using data for correcting attenuation (such as an attenuation map) generated based on a CT image (hereinafter referred to as attenuation correction).

In image capturing using a PET apparatus, a subject is imaged while breathing. However, because a bodily movement caused by the respiration results in an artifact, such an apparatus scans the subject in a manner synchronized with the respiration of the subject.

However, in attenuation correction using a CT image, the PET-CT apparatus described above does not give any particular consideration to the synchronization of the raw PET data with the respiratory phase. Therefore, the conventional PET-CT apparatus may perform the attenuation correction using a CT image scanned in a respiratory phase different from the respiratory phase at the time at which raw PET data is acquired.

DETAILED DESCRIPTION

Figure 1:
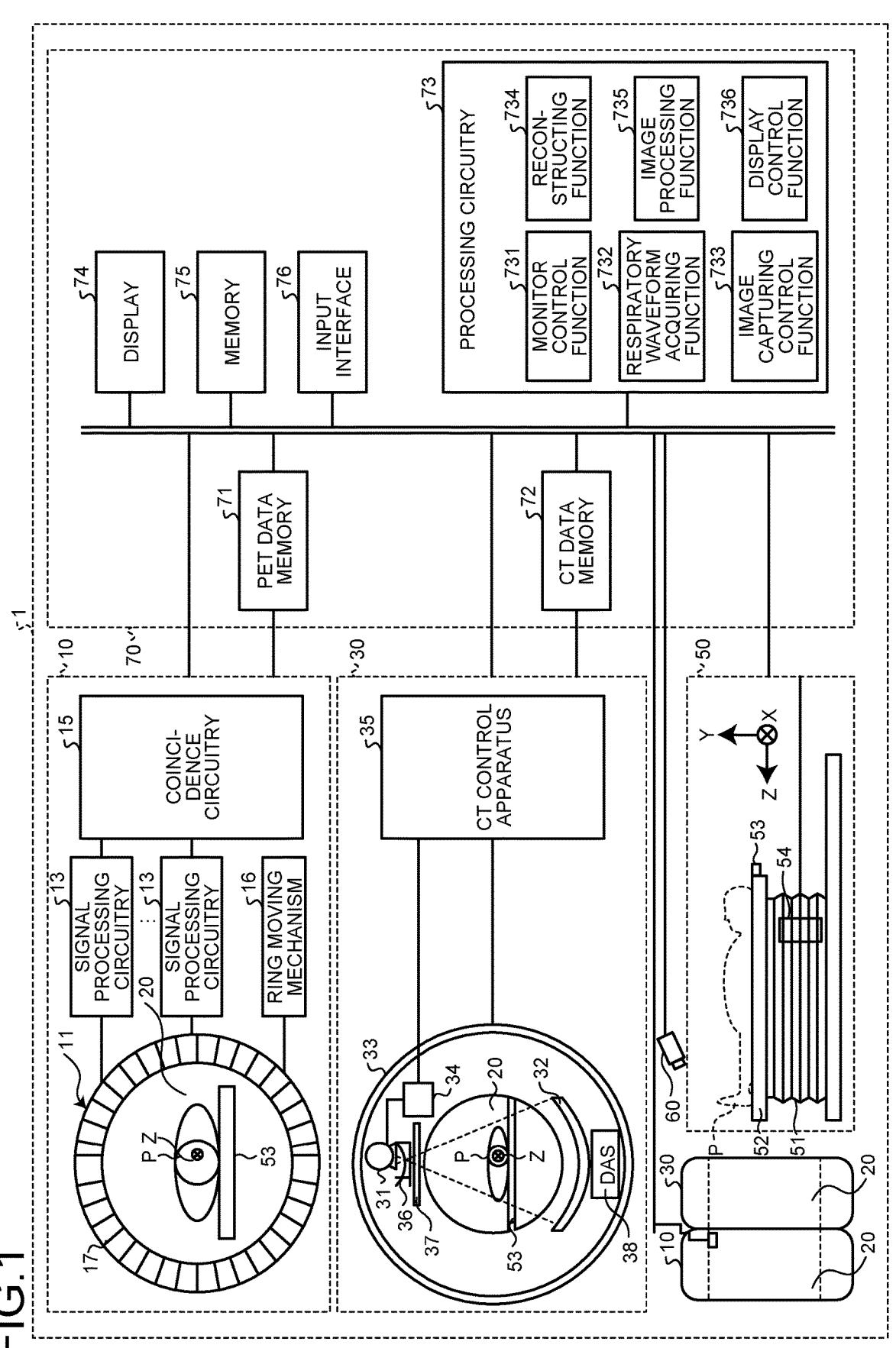
FIG. 1 is a schematic view illustrating a configuration of a PET-CT apparatus according to an embodiment.

A problem to be solved by an embodiment disclosed herein and in the drawings is to provide a PET-CT apparatus, a medical image processing method, and a non-transitory computer-readable medium capable of improving the image quality of a PET image by using a CT image in attenuation correction. The problem to be solved by the embodiment disclosed herein and in the drawings is, however, not limited to that described above. The problem corresponding to the effect achieved by each configuration disclosed in the embodiment to be described below can be regarded as another problem.

A PET-CT apparatus according to the embodiment includes processing circuitry. The processing circuitry scans a subject to acquire an attenuation-correcting CT image, identifies a respiratory phase of the subject when the CT image is scanned, acquires PET scan data that is based on a gamma ray emitted from the subject, generates gate data by gating the PET scan data based on the respiratory phase, and reconstructs a PET image based on the CT image and the gate data.

An embodiment of a PET-CT apparatus, a medical image processing method, and a non-transitory computer-readable medium according to the present invention will now be explained with reference to the accompanying drawings.

FIG. 1 is a schematic view illustrating a configuration of a PET-CT apparatus 1 according to the embodiment. As illustrated in FIG. 1, the PET-CT apparatus 1 includes a PET gantry 10, a CT gantry 30, a couch 50, an infrared camera 60, and a console 70. Typically, the PET gantry 10, the CT gantry 30, the couch 50, and the infrared camera 60 are installed in the same examination room. The console 70 is installed in a control room adjacent to the examination room.

The PET gantry 10 is an image capturing apparatus that performs a PET scan on a subject P. The CT gantry 30 is an image capturing apparatus that performs a CT scan on the subject P. The couch 50 movably supports a couchtop 53 on which the subject P to be imaged is laid. The console 70 is a computer that controls units such as the PET gantry 10, the CT gantry 30, and the couch 50.

The PET gantry 10 includes, for example, a plurality of PET detector rings, signal processing circuitry 13, coincidence circuitry 15, and a ring moving mechanism 16. FIG. 1 illustrates one PET detector ring 11, but in the actual PET gantry 10, a plurality of PET detector rings are mounted in a manner movable with respect to the couchtop 53 on which the subject P is laid, along a central axis direction (Z direction) inside a bore 20 into which the couchtop 53 is to be inserted. The signal processing circuitry 13 and the coincidence circuitry 15 are provided for each of the PET detector rings, for example. The ring moving mechanism 16 supports each of the PET detector rings in a manner movable along the direction of the central axis (Z direction) of the bore 20. The PET gantry 10 and the CT gantry 30 may be housed inside the same housing.

Each of the PET detector rings 11 includes a plurality of gamma ray detectors 17 that are arranged along a circumference about the central axis Z. The gamma ray detectors 17 are also referred to as PET detectors. An image field of view (FOV) is set to the opening of the PET detector rings 11. The subject P is positioned in such a manner that a target region of the subject P is positioned within the image FOV. A drug labeled with positron-emitting radionuclide is administered to the subject P. The positrons emitted from the positron-emitting radionuclides cause pair annihilation with nearby electrons. This pair annihilation generates pair annihilation gamma rays. The gamma ray detector 17 detects the pair annihilation gamma rays emitted from the internal of the subject P. The gamma ray detector 17 generates an electrical signal corresponding to the amount of the detected pair annihilation gamma rays. For example, the gamma ray detector 17 includes a plurality of scintillators and a plurality of photomultiplier tubes. The scintillators are caused to emit scintillation light by receiving the pair annihilation gamma rays derived from the radioisotopes in the subject P. Each of the photomultiplier tubes generates an electrical signal based on the light amount of the scintillation light. The generated electrical signals are supplied to the signal processing circuitry 13.

The signal processing circuitry 13 generates single-event data based on each electrical signal output from the gamma ray detector 17. Specifically, the signal processing circuitry 13 applies, for example, a detection time measuring process, a position calculating process, and an energy calculating process to the electrical signal. The signal processing circuitry 13 is implemented with an application-specific integrated circuit (ASIC), a field-programmable gate array (FPGA), another complex programmable logic device (CPLD), or a simple programmable logic device (SPLD) enabled to execute the detection time measuring process, the position calculating process, and the energy calculating process.

In the detection time measuring process, the signal processing circuitry 13 measures the time at which a gamma ray is detected by the gamma ray detector 17. Specifically, the signal processing circuitry 13 monitors the wave height of the electrical signal from the gamma ray detector 17, and measures the time at which the wave height exceeds a preset threshold as the detection time. To put in other words, the signal processing circuitry 13 electrically detects the pair annihilation gamma rays by detecting that the wave height exceeds the threshold. In the position calculating process, the signal processing circuitry 13 calculates positions on which the pair annihilation gamma rays are incident, based on the electrical signal from the gamma ray detector 17. The incident positions of the pair annihilation gamma rays correspond to the coordinates corresponding to the positions of the scintillators on which the pair annihilation gamma rays are incident. In the energy calculating process, the signal processing circuitry 13 calculates the energy of the detected pair annihilation gamma rays, based on the electrical signal from the gamma ray detector 17.

The detection time data, the position coordinate data, and the energy data related to a single event are associated with one another. This combination of the energy data, the position coordinate data, and the detection time data related to a single event is referred to as single-event data. Such single-event data is generated every time the pair annihilation gamma rays are detected. The generated single-event data is supplied to the coincidence circuitry 15.

The coincidence circuitry 15 performs a coincidence counting process of single-event data from the signal processing circuitry 13. As a hardware resource, the coincidence circuitry 15 is implemented with an ASIC, an FPGA, a CPLD, or an SPLD enabled to perform the coincidence counting process. In the coincidence counting process, the coincidence circuitry 15 repeatedly identifies single-event data related to two single events taking place within a predetermined time frame, from the pieces of single-event data that are repeatedly supplied thereto. This pair of single events that is presumably derived from the pair annihilation gamma rays emitted from the same pair annihilation point. This single-event pair is collectively referred to as coincidence event. A pair of the gamma ray detectors 17 (more specifically, a pair of scintillators) having detected these pair annihilation gamma rays is referred to as line of response (LOR). The event data related to the pair of events corresponding to an LOR is referred to as coincidence event data. The coincidence event data and single-event data are transferred to the console 70. The coincidence event data is also used in reconstructing a PET image. Hereinafter, the coincidence event data will also be referred to as raw PET data. Raw PET data is one example of PET scan data.

In the configuration described above, the signal processing circuitry 13 and the coincidence circuitry 15 are included in the PET gantry 10, but the embodiment is not limited thereto. For example, the coincidence circuitry 15, or both of the signal processing circuitry 13 and the coincidence circuitry 15 may be included in an apparatus separate from the PET gantry 10. Furthermore, one coincidence circuitry 15 may be provided for a plurality of the pieces of signal processing circuitry 13 mounted on the PET gantry 10, or pieces of the signal processing circuitry 13 mounted on the PET gantry 10 may be grouped into a plurality of groups, and one coincidence circuitry 15 may be provided for each of the groups.

The ring moving mechanism 16 moves the PET detector rings along the direction of the central axis of the bore 20 (Z direction), under the control of an image capturing control function 733 in processing circuitry 73 described later. The ring moving mechanism 16 includes, for example, a ring support mechanism that supports the PET detector rings in a movable manner along the direction of the central axis of the bore 20 (Z direction), a moving mechanism that moves the PET detector rings in the ring support mechanism, and a driving mechanism that moves the moving mechanism. The ring support mechanism is implemented with a linear bearing disposed along the direction of the central axis of the bore 20 (Z direction) in the PET gantry 10, for example. The means for implementing the ring support mechanism is not limited to the linear bearing, and other various types of known bearings may be used, for example. The rail of the linear bearing is provided on a fixed frame of the PET gantry 10, in a manner extending along the direction of the central axis of the bore 20 (Z direction). The linear bearing includes blocks running along the rail, and frames each holding corresponding one of the PET detector rings in a ring-like shape are mounted on the blocks.

The moving mechanism is implemented with a plurality of racks and pinions corresponding to the respective PET detector rings. The means for implementing the moving mechanism is not limited to racks and pinions, and any known apparatus such as ball screws may also be used, as appropriate. The rack gears in the racks and pinions are disposed along the direction of the central axis of the bore 20 (Z direction), and are connected to the holding frames corresponding to the respective PET detector rings. The pinion gears are meshed with the respective rack gears. Each of the pinion gears may be provided with a rotary encoder that measures the number of revolutions of the pinion gear, for example. At this time, the output from the rotary encoder is input to the processing circuitry 73.

The driving mechanism is implemented with a motor, for example. A rotation shaft of the motor is connected to the pinion gears via various gears, for example. When no rotary encoders are provided on the pinion gears, the rotation shaft of the motor or the various gears may be provided with a rotary encoder to measure the number of revolutions of the rotation shaft, for example. At this time, the output from the rotary encoder is input to the processing circuitry 73. The motor is driven in response to a control signal from the image capturing control function 733. As the motor is rotated to cause the pinion gears to rotate, the rack gears are caused to move along the direction of the central axis of the bore 20 (Z direction). As the rack gears are caused to move, the PET detector rings are caused to move along the direction of the central axis of the bore 20 (Z direction).

As illustrated in FIG. 1, the CT gantry 30 includes a CT image capturing mechanism. The CT image capturing mechanism performs a CT scan of the subject P. The CT image capturing mechanism may also capture an image of the subject P by executing X-ray scan. The CT image capturing mechanism includes an X-ray tube 31, an X-ray detector 32, a rotating frame 33, a high-voltage X-ray apparatus 34, a CT control apparatus 35, a wedge 36, a collimator 37, and a data acquisition system (DAS) 38.

The X-ray tube 31 generates X-rays. Specifically, the X-ray tube 31 includes a vacuum tube holding a cathode that emits thermal electrons, and an anode that emits X-rays by receiving the thermal electrons flying from the cathode. The X-ray tube 31 is connected to the high-voltage X-ray apparatus 34 via a high-voltage cable. The high-voltage X-ray apparatus 34 applies a tube voltage between the cathode and the anode. With this application of the tube voltage, thermal electrons are caused to fly from the cathode toward the anode. These thermal electrons flying from the cathode to the anode generates a tube current. With the application of the high voltage with the high-voltage X-ray apparatus 34 and supply of a filament current, thermal electrons fly from the cathode toward anode, and collide with the anode. As a result, X-rays are generated.

The X-ray detector 32 detects the X-rays emitted from the X-ray tube 31 and passed through the subject P. The X-ray detector 32 outputs an electrical signal corresponding to the detected X-ray dose to the DAS 38. The X-ray detector 32 has a structure in which a plurality of rows of X-ray detecting elements are arranged in the slice direction (also referred to as row direction), each rows of the X-ray detecting elements including a plurality of X-ray detecting elements arranged in the channel direction. The X-ray detector 32 is an indirect conversion detector including a grid, a scintillator array, and a photosensor array, for example. The scintillator array includes a plurality of scintillators. A scintillator outputs light having a light amount corresponding to the X-ray dose incident thereon. The grid is disposed on a surface of the scintillator array on which the X-rays are incident. The grid includes X-ray shields that absorb the scattered X-rays. The photosensor array converts the light output from the scintillator, into an electrical signal corresponding to the light amount of the light. As the photosensor, a photodiode or a photomultiplier tube is used, for example. The X-ray detector 32 may also be implemented with a direct conversion detector (semiconductor detector) having a semiconductor element that converts the incident X-ray into an electrical signal.

The rotating frame 33 is a ring-shaped frame that supports the X-ray tube 31 and the X-ray detector 32 in a manner rotatable about the rotational axis Z. Specifically, the rotating frame 33 supports the X-ray tube 31 and the X-ray detector 32 in a manner facing each other. The rotating frame 33 is supported by a fixing frame (not illustrated) in a manner rotatable about the rotational axis Z. The rotating frame 33 is rotated about the rotational axis Z under the control of the CT control apparatus 35. As a result, the X-ray tube 31 and the X-ray detector 32 rotate about the rotational axis Z. The rotating frame 33 receives power from the driving mechanism of the CT control apparatus 35, and is caused to rotate at a certain angular speed about the rotational axis Z. The image FOV is set to the opening of the rotating frame 33.

In the embodiment, the rotational axis of the rotating frame 33 not tilted or the longitudinal direction of the couchtop 53 of the couch 50 is defined as a Z-axis direction; the axial direction perpendicular to the Z-axis direction and horizontal with respect to the floor surface is defined as an X axis direction; and the axial direction perpendicular to the Z direction and vertical with respect to the floor surface is defined as a Y axis direction.

The high-voltage X-ray apparatus 34 includes electric circuitry such as a transformer and a rectifier. The high-voltage X-ray apparatus 34 includes a high-voltage generator that generates a high voltage to be applied to the X-ray tube 31 and a filament current to be supplied to the X-ray tube 31, and an X-ray controller that controls the output voltage based on the X-ray to be emitted from the X-ray tube 31. The high-voltage generator may be a transformer generator or an inverter generator. The high-voltage X-ray apparatus 34 may be provided to the rotating frame 33 in the CT gantry 30, or may be provided to the fixing frame (not illustrated) inside the CT gantry 30.

The wedge 36 adjusts the X-ray dose with which the subject P is irradiated. Specifically, the wedge 36 attenuates the X-rays so that the X-ray dose from the X-ray tube 31 with which the subject P is to be irradiated has a predetermined distribution. As the wedge 36, a plate made of a metal, e.g., aluminum is used. Examples of the wedge 36 include a wedge filter and a bow-tie filter.

The collimator 37 restricts the area to be irradiated with the X-rays passed through the wedge 36. The collimator 37 supports a plurality of lead plates, which block X-rays, in a slidable manner, to adjust the shape of the slit formed by the lead plates.

The data acquisition system (DAS) 38 reads an electrical signal corresponding to an X-ray dose detected by the X-ray detector 32, from the X-ray detector 32. The DAS 38 amplifies the read electrical signal by a variable amplification factor. The DAS 38 collects CT raw data (e.g., a sinogram) having digital values corresponding to the X-ray doses across a view period, by calculating an integral of amplified electrical signals over the view period. The DAS 38 is implemented, for example, with an ASIC having a circuit element capable of generating CT raw data. The CT raw data is transmitted to the console 70 via a contactless data transmitting apparatus, for example.

The CT control apparatus 35 controls units, for example, the high-voltage X-ray apparatus 34 and the DAS 38 to execute a CT scan, with the image capturing control function 733 of the processing circuitry 73 in the console 70. The CT control apparatus 35 includes processing circuitry having a central processing unit (CPU), for example, and a driving mechanism such as a motor and an actuator. The processing circuitry includes, as hardware resources, a processor, such as a CPU or a micro-processing unit (MPU), and a memory, such as a read-only memory (ROM) and a random access memory (RAM). The CT control apparatus 35 may also be implemented with an ASIC, an FPGA, a CPLD, or an SPLD.

There are various types of CT gantries, and any of such types may be used as the CT gantry 30. Some examples of the types of CT gantries are a rotate-rotate gantry (the third-generation CT) and a stationary-rotate gantry (the fourth-generation CT). While the former example includes an X-ray generator and an X-ray detector integrated as one unit that is rotated about a subject, the latter includes a large number of X-ray detecting elements arranged in a ring-like shape, and only the X-ray generator is rotated about the subject.

As illustrated in FIG. 1, the couch 50 supports the subject P to be scanned, and moves the subject laid thereon. The couch 50 is shared between the PET gantry 10 and the CT gantry 30.

The couch 50 includes a base 51, a support frame 52, the couchtop 53, and a couch driving apparatus 54. The base 51 is installed on the floor surface. The base 51 is a housing supporting the support frame 52 movably along the vertical directions with respect to the floor surface (in the Y-axis directions). The support frame 52 is a frame provided on top of the base 51. The support frame 52 supports the couchtop 53 slidably along the central axis Z. The couchtop 53 is a flexible plate on which the subject P is laid.

The couch driving apparatus 54 is housed inside the housing of the couch 50. The couch driving apparatus 54 is a motor or an actuator that generates a force for moving the support frame 52 and the couchtop 53 on which the subject P is laid. The couch driving apparatus 54 is actuated under the control of the console 70, for example.

The PET gantry 10 and the CT gantry 30 are disposed in such a manner that the central axis Z of the opening of the PET gantry 10 and the central axis Z of the opening of the CT gantry 30 are substantially in alignment. The couch 50 is disposed in such a manner that the longitudinal axis of the couchtop 53 is in parallel with the central axis Z of the openings of the PET gantry 10 and the CT gantry 30. The CT gantry 30 and the PET gantry 10 are installed in the order of the CT gantry 30 and the PET gantry 10, from the side nearer to the couch 50, for example. In the example explained below, a CT scan is executed by the CT gantry 30 and then a PET scan is executed by the PET gantry 10, but the order in which the CT scan and the PET scan are executed may be reversed.

As illustrated in FIG. 1, the infrared camera 60 is provided at a position from which an image of subject P laid on the couch 50 can be captured. The infrared camera 60 includes an infrared imaging element, for example, and generates and outputs data visualizing the infrared emitted from an object. The infrared camera 60 is one example a monitoring apparatus that monitors the subject P.

Figure 2:
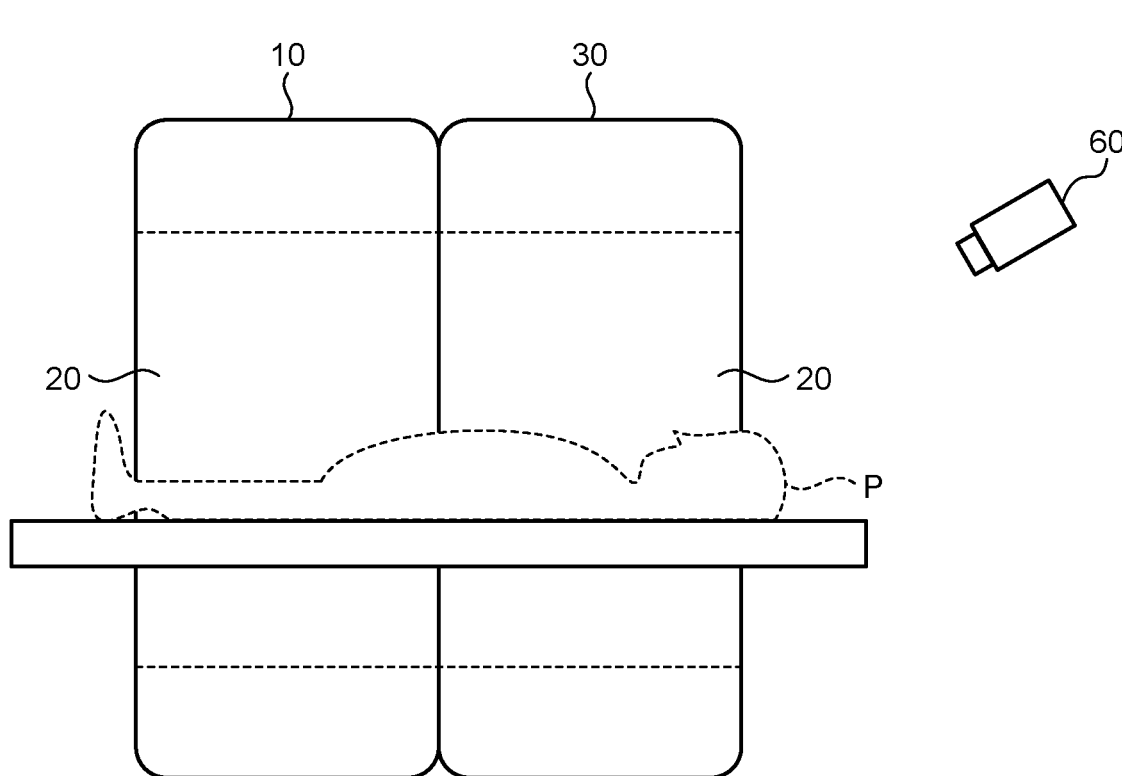
FIG. 2 is a schematic view illustrating one example of the position on which an infrared camera is disposed with respect to a CT gantry and a PET gantry in the embodiment.

Specifically, the infrared camera 60 is provided at a position and an angle from which an image of the top surface of the couchtop 53 inside the bore 20 can be captured, as illustrated in FIG. 2. FIG. 2 is a schematic view illustrating one example of the position on which the infrared camera 60 is disposed with respect the CT gantry 30 and the PET gantry 10.

In FIG. 2, the infrared camera 60 captures an image of a region of the subject P laying on the couchtop 53, the region being where the shape and the temperature change as the respiration takes place, e.g., the chest or the abdomen of the subject P. Data of the image captured by the infrared camera 60 is used for deriving a respiratory waveform of the subject P.

In the manner described above, by using the infrared camera 60, the respiratory waveform can be derived from the data output from the infrared camera 60 even when the examination room is dark, for example. Furthermore, by using the infrared camera 60, the respiratory waveform can be derived from the data output from the infrared camera 60 even when a drape or the like is placed on the subject P, for example. Therefore, use of the infrared camera 60 can improve convenience.

In the example illustrated in FIGS. 1 and 2, the infrared camera 60 is provided outside of the CT gantry 30 and the PET gantry 10, but the configuration is not limited thereto. For example, the infrared camera 60 may also be provided around the opening of the CT gantry 30 or the PET gantry 10, or inside the bore 20.

Referring back to FIG. 1, the console 70 includes a PET data memory 71, a CT data memory 72, processing circuitry 73, a display 74, a memory 75, and an input interface 76. For example, the PET data memory 71, the CT data memory 72, the processing circuitry 73, the display 74, the memory 75, and the input interface 76 exchange data with one another over a bus.

The PET data memory 71 is a storage storing therein single-event data and coincidence event data received from the PET gantry 10. The PET data memory 71 is a storage such as a hard-disk drive (HDD), a sold-state drive (SSD), or an integrated circuit (IC) storage.

The CT data memory 72 is a storage storing therein the CT raw data received from the CT gantry 30. The CT data memory 72 is a storage such as an HDD, an SSD, or an IC storage.

The processing circuitry 73 includes a processor such as a CPU, an MPU, or graphics processing unit (GPU), and a memory such as a ROM and a RAM, as hardware resources. The processing circuitry 73 implements functions such as a monitor control function 731, a respiratory waveform acquiring function 732, the image capturing control function 733, a reconstructing function 734, an image processing function 735, and a display control function 736, by executing various computer programs read from the memory. In other words, the processing circuitry 73 corresponds to a processor that reads a computer program from the memory, and executes the computer program, to implement the function corresponding to the computer program. To put in other words, the processing circuitry 73 having read each computer program come to have the function corresponding to the read computer program.

The monitor control function 731, the respiratory waveform acquiring function 732, the image capturing control function 733, the reconstructing function 734, the image processing function 735, and the display control function 736 may be implemented by the processing circuitry 73 on one circuit board, or implemented in a manner distributed across the processing circuitry 73 distributed across a plurality of circuit boards. The processing circuitry 73 implementing the monitor control function 731, the respiratory waveform acquiring function 732, the image capturing control function 733, the reconstructing function 734, the image processing function 735, and the display control function 736 correspond to a first acquiring unit, a first identifying unit, a second acquiring unit, a gating processing unit, a reconstruction processing unit, and a third acquiring unit. More specifically, the first acquiring unit corresponds to the image capturing control function 733 and the reconstructing function 734. The second acquiring unit, the gating processing unit, and the reconstruction processing unit correspond to the reconstructing function 734. The third acquiring unit corresponds to the respiratory waveform acquiring function 732.

In the monitor control function 731, the processing circuitry 73 controls the operation of the infrared camera 60. Specifically, the processing circuitry 73 monitors the subject P by causing the infrared camera 60 to operate simultaneously with the operation of the PET-CT apparatus 1. For example, when the PET-CT apparatus 1 starts capturing an image, the processing circuitry 73 causes the infrared camera 60 to operate, to start monitoring the subject P. When the scanning operation of the PET-CT apparatus 1 is finished, the processing circuitry 73 also stops monitoring the subject P by stopping the infrared camera 60.

In the monitor control function 731, the processing circuitry 73 also acquires data output from the infrared camera 60, and retains the data in the memory 75 or the like, as the monitoring data of the subject P. For example, the processing circuitry 73 retains pieces of monitoring data output from the infrared camera 60 during the CT scan and the PET scan, separately. The processing circuitry 73 also transfers the pieces of monitoring data acquired in the CT scan and the PET scan, respectively, to the respiratory waveform acquiring function 732.

In the respiratory waveform acquiring function 732, the processing circuitry 73 detects respiratory dynamics such as exhalation and inhalation of the subject P, from the monitoring data acquired by the monitor control function 731, and acquires a respiratory waveform that is a chronological representation of the respiratory dynamics. Specifically, the processing circuitry 73 acquires the respiratory waveform of the subject P during the CT scan (hereinafter referred to as CT respiratory waveform), from the monitoring data acquired by the CT scan. The processing circuitry 73 also acquires the respiratory waveform of the subject P during the PET scan (hereinafter referred to as PET respiratory waveform), from the monitoring data acquired by the PET scan.

The method of detecting the respiratory dynamics is not limited to a particular method, and known methods, such as a respiration monitoring technology using moving image processing, may be used. For example, in the embodiment, the monitoring data output from the infrared camera 60 represents a difference between temperatures of the body region of the subject P and of regions other than the body region. Therefore, the processing circuitry 73 may detect the respiratory dynamics of the subject P based on a chronological change in the image in the area along the boundary between the body region and the other region (temperature change). Furthermore, for example, it is known that the temperatures of body parts such as the chest or the abdomen change as the respiration takes place. Therefore, the processing circuitry 73 may also detect respiratory dynamics based on the chronological change in the image of the body region of the subject P represented in the monitoring data (temperature change).

In the respiratory waveform acquiring function 732, the processing circuitry 73 also acquires the start time and the end time of a CT scan, by cooperating with the image capturing control function 733, and stores the start time and the end time in a manner associated with the CT respiratory waveform. For example, the respiratory waveform acquiring function 732 records the start time and the end time of a CT scan, in a manner associated with the time axis of the CT respiratory waveform.

In the image capturing control function 733, the processing circuitry 73 controls the CT gantry 30 and the couch 50 synchronously to execute a CT scan. The processing circuitry 73 also controls a CT scan executed by the CT gantry 30, by cooperating with the CT control apparatus 35 and the like. The processing circuitry 73 also controls the PET gantry 10 and the couch 50 synchronously to execute a PET scan. The processing circuitry 73 also controls the PET scan executed by the PET gantry 10 by cooperating with the coincidence circuitry 15. When a CT scan and a PET scan are to be executed successively, the processing circuitry 73 controls the CT gantry 30, the PET gantry 10, and the couch 50 synchronously. For example, the processing circuitry 73 executes a CT scan to acquire an attenuation-correcting CT image that is to be used in attenuation correction of the PET image.

In the reconstructing function 734, the processing circuitry 73 reconstructs a CT image representing a spatial distribution of the CT values related to the subject P, based on the CT raw data obtained from the CT scan. The processing circuitry 73 also reconstructs a PET image representing a distribution of the positron-emitting radionuclide administered to the subject P, based on the coincidence event data acquired by a PET scan. The processing circuitry 73 is also capable of generating an alignment image (CT scan image) related to the CT, based on the CT raw data, and of generating an alignment image related to the PET, based on the raw PET data.

In the reconstructing function 734, the processing circuitry 73 reconstructs a PET image applied with attenuation correction based on the attenuation-correcting CT image acquired in the CT scan and the raw PET data. Specifically, the processing circuitry 73 identifies the respiratory phase of the subject P during the time in which the CT scan is executed (hereinafter also referred to as CT respiratory phase), based on the start time and the end time of the CT scan, recorded in a manner associated with the CT respiratory waveform.

The processing circuitry 73 generates gating data by gating the raw PET data based on the identified CT respiratory phase. Specifically, the processing circuitry 73 generates the gating data by extracting raw PET data acquired in the period corresponding to the CT respiratory phase, based on the PET respiratory waveform at the time of the PET scan. The processing circuitry 73 then reconstructs a PET image applied with attenuation correction based on the attenuation-correcting CT image acquired in the CT scan, and on the gating data.

In the manner described above, the processing circuitry 73 extracts the raw PET data (gate data) acquired in the respiratory phase that is substantially equivalent to the respiratory phase at the time of the CT image scan, and reconstructs a PET image based on the CT image and the gate data. In this manner, because the processing circuitry 73 can improve the precision in the synchronization of the respiratory phase in the CT image and the raw PET data, it is possible to acquire a PET image applied with attenuation correction, with the effect of respiratory movement suppressed.

As the image reconstruction algorithm, a known image reconstruction algorithm such as filtered back projection (FBP) or iterative reconstruction may be used. Furthermore, as a gating method, a known technology such as retrospective gating or prospective gating may be used. As an attenuation correction method, a known technology such as CT-based attenuation correction (CTAC), converting a CT image to an attenuation map (p-MAP) and applying correction, may be used.

In the image processing function 735, the processing circuitry 73 applies various types of image processing to the CT image and the PET image reconstructed by the reconstructing function 734. For example, the processing circuitry 73 generates a display image by applying three-dimensional image processing such as volume rendering, surface volume rendering, pixel value projection, multi-planer reconstruction (MPR), curved MPR (CPR) to the CT image and the PET image. Furthermore, for example, the processing circuitry 73 generates a composite image by combining the PET image and the CT image.

In the display control function 736, the processing circuitry 73 generates various types of display information, and displays the generated display information on the display 74. For example, the processing circuitry 73 generates the display information by mapping the positions of the PET detector rings 11 to the information related to the subject P. The display information is information indicating a relative positional relation between the PET detector rings 11 and the subject P lying on the couchtop 53, for example. At this time, the display information includes ring display objects representing the PET detector rings, respectively, as the positions of the respective PET detector rings 11. The display information may also include the position of the X-ray detector 32 with respect to the subject P.

The display information may also include information indicating a region of the subject P, the region being a region an image of which is to be captured (e.g., a frame in a dotted line or an imaging mode representing the region of interest), based on a user instruction via the input interface 76 or the region to be examined specified in an examination order output from a radiology information system (RIS) or a hospital information system (HIS).

The display 74 displays various types of information under the control of the display control function 736 in the processing circuitry 73. As the display 74, for example, a cathode ray tube (CRT) display, a liquid crystal display (LCD), an organic electro luminescence display (OELD), a light-emitting diode (LED) display, a plasma display, or any other display that is known in this technical field may be used as appropriate. The display 74 may be implemented with a desktop display, or a tablet terminal capable of wirelessly communicating with the console 70. The display 74 corresponds to a display unit.

The memory 75 is a storage, such as a HDD, SSD, or an integrated circuit storage, storing therein various types of information. The memory 75 may be a drive or the like reading and writing various types of information from and to a portable storage medium such as a compact disc (CD)-ROM drive, a digital versatile disc (DVD) drive, or a flash memory.

The memory 75 stores therein various computer programs and various types of data related to the executions of the monitor control function 731, the respiratory waveform acquiring function 732, the image capturing control function 733, the reconstructing function 734, the image processing function 735, and the display control function 736, for example. The memory 75 also stores therein monitoring data acquired by the monitor control function 731, for example. The memory 75 also stores therein images such as the CT image or the PET image reconstructed by the reconstructing function 734, for example.

The input interface 76 receives various input operations (e.g., instructions for executing a CT scan and a PET scan, a selection of a range to be captured in an image) from a user, converts the input operations into electrical signals, and outputs the signals to the processing circuitry 73. As the input interface 76, for example, a mouse, a keyboard, a trackball, a switch, a button, a joystick, a touchpad, and a touch panel display may be used, as appropriate. In the embodiment, the input interface 76 is not limited to those having physical operation parts such as a mouse, a keyboard, a trackball, a switch, a button, a joystick, a touchpad, and a touch panel display. Another example of the input interface 76 includes electrical signal processing circuitry receiving an electrical signal corresponding to an input operation from an external input device that is provided separately from the apparatus, and outputting the electrical signal to the processing circuitry 73. Furthermore, the input interface 76 may also be configured as a tablet terminal capable of communicating with the console 70 wirelessly. The input interface 76 corresponds to an input unit.

The overall configuration of the PET-CT apparatus 1 has been explained so far. An exemplary operation of the PET-CT apparatus 1 will now be explained with reference to FIG. 3.

Figure 3:
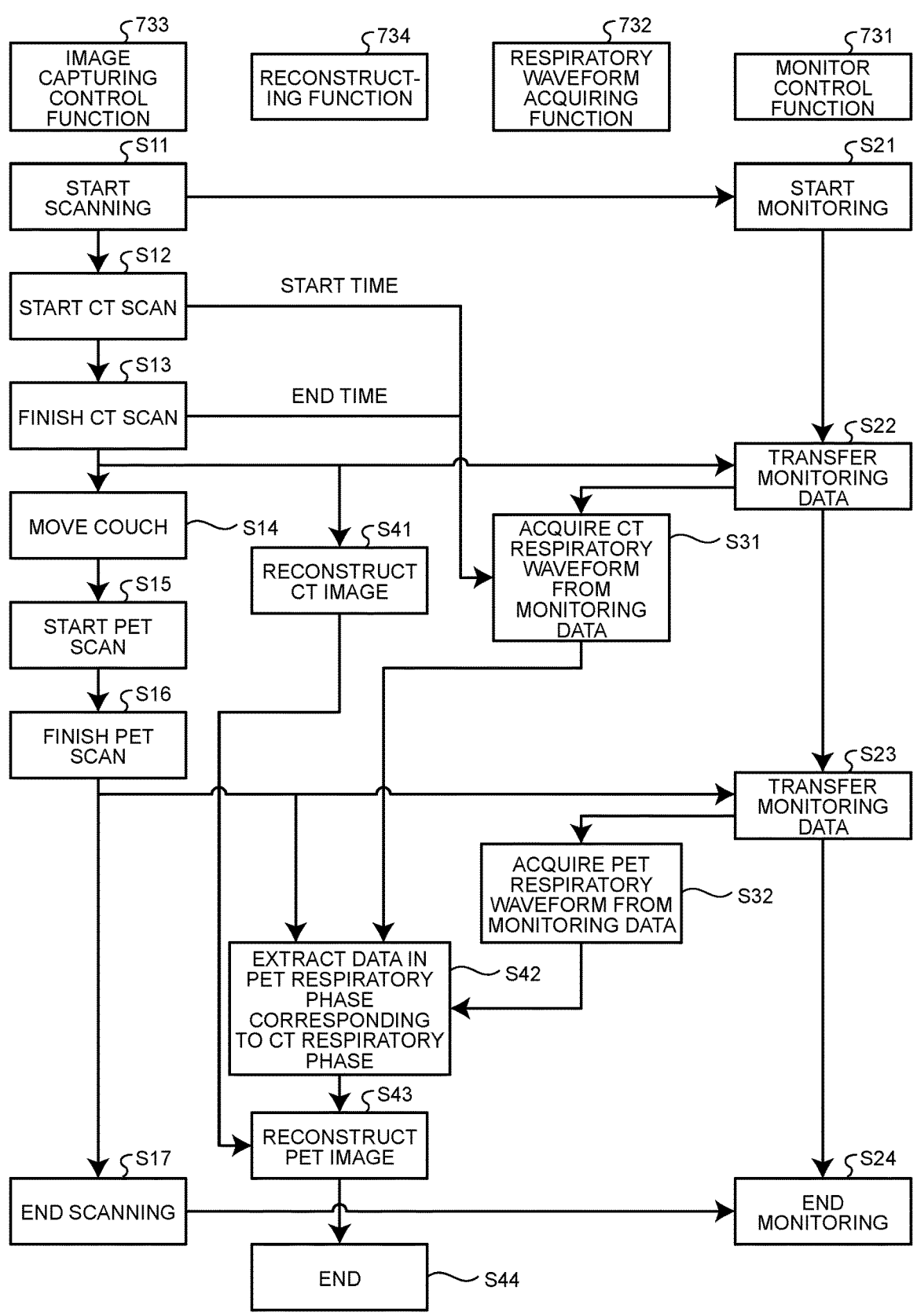
FIG. 3 is a sequence chart illustrating one example of a scanning operation performed by the PET-CT apparatus according to the embodiment.

FIG. 3 is a sequence chart illustrating one example of a scanning operation performed by the PET-CT apparatus 1. In FIG. 3, a scanning operation for acquiring an attenuation-correcting CT image and reconstructing a PET image using the CT image will be explained. In the explanation below, a function implemented by the processing circuitry 73 will be explained as a subject executing the corresponding operation.

To begin with, the image capturing control function 733 causes the PET-CT apparatus 1 to execute a scanning operation, in response to an operation instruction or the like entered via the input interface 76 (Step S11). The monitor control function 731 then causes the infrared camera 60 to start monitoring the subject P, simultaneously with the start of the scanning operation at Step S11 (Step S21).

The image capturing control function 733 then starts the CT scan by controlling the CT gantry 30 and the couch 50 synchronously (Step S12). For example, an operator or a technician of the PET-CT apparatus 1 starts the CT scan at the timing of a predetermined respiratory phase, such as at the timing of the maximum expiration or the maximum inspiration, by guiding the subject P to breathe at the start of the CT scan. The image capturing control function 733 notifies the respiratory waveform acquiring function 732 of the start time indicating the time at which the CT scan is started, at the timing at which the CT scan is started.

Once the CT scan is finished (Step S13), the image capturing control function 733 moves the couch 50 so as to execute a PET scan (Step S14). The image capturing control function 733 also notifies the respiratory waveform acquiring function 732 of the end time indicating the time at which the CT scan has finished, at the timing at which the CT scan has finished.

At the timing at which the CT scan is finished, the monitor control function 731 also transfers the monitoring data having been acquired up to the point in time to the respiratory waveform acquiring function 732 (Step S22). The respiratory waveform acquiring function 732 acquires the CT respiratory waveform from the monitoring data, transferred at Step S22 (Step S31). The respiratory waveform acquiring function 732 also records the start time and the end time notified by the image capturing control function 733 to the CT respiratory waveform.

The reconstructing function 734 identifies the CT respiratory phase of the time when the CT scan has been executed, based on the CT respiratory waveform acquired at Step S31. For example, when the CT scan has been executed at the timing of expiration, the reconstructing function 734 identifies the expiratory phase as the CT respiratory phase. The timing for identifying the CT respiratory phase is not limited thereto. For example, the reconstructing function 734 may identify the CT respiratory phase after the PET scan is finished.

As the CT scan is finished, the reconstructing function 734 also reconstructs a CT image from the CT raw data acquired by the CT scan, to acquire an attenuation-correcting CT image (Step S41).

After moving the couch 50 at Step S14, the image capturing control function 733 starts the PET scan (Step S15). Once the PET scan is finished (Step S16), the image capturing control function 733 ends the scanning operation of the PET-CT apparatus 1 (Step S17).

At the timing at which the PET scan is finished, the monitor control function 731 also transfers the monitoring data having been acquired up to the point in time to the respiratory waveform acquiring function 732 (Step S23). The monitor control function 731 then causes the infrared camera 60 to end monitoring the subject P, simultaneously with the end of the scan at Step S17 (Step S24).

The respiratory waveform acquiring function 732 acquires the PET respiratory waveform from the monitoring data, transferred at Step S23 (Step S32). The reconstructing function 734 then extracts gating data in the respiratory phase (hereinafter referred to as PET respiratory phase) corresponding to the CT respiratory phase from the raw PET data acquired by the PET scan, based on the PET respiratory waveform corresponding to the time of the PET scan (Step S42).

The reconstructing function 734 then applies attenuation correction based on the attenuation-correcting CT image and the gating data, to reconstruct a PET image (Step S43), and ends the process (Step S44).

Figure 4:
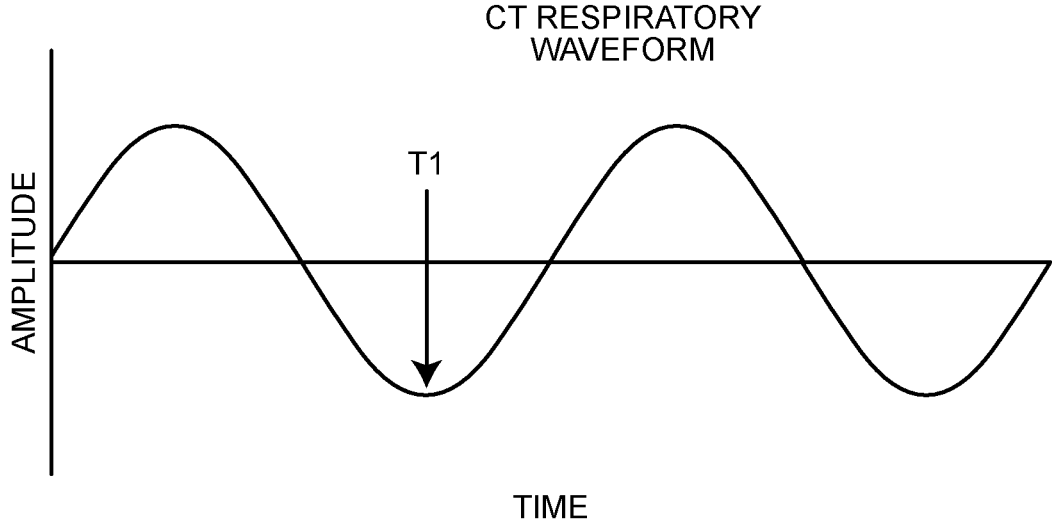
FIG. 4 is a schematic view illustrating one example of a CT respiratory waveform according to the embodiment.
Figure 5:
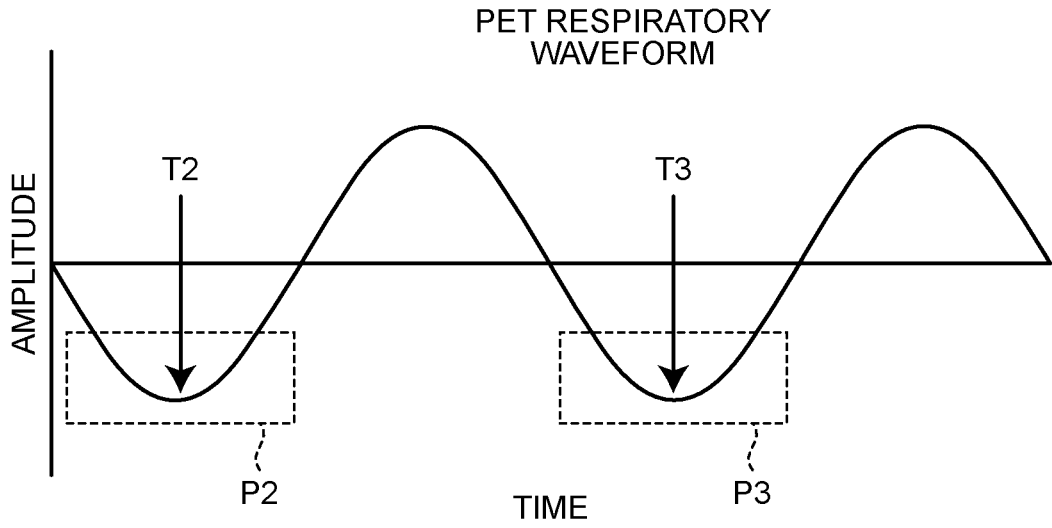
FIG. 5 is a schematic view illustrating one example of a PET respiratory waveform according to the embodiment.

The process at Step S42 will now be explained with reference to FIGS. 4 and 5. FIG. 4 is a schematic view illustrating one example of a CT respiratory waveform. FIG. 5 is a schematic view illustrating one example of a PET respiratory waveform.

As illustrated in FIGS. 4 and 5, a respiratory waveform is chronological waveform data representing the respiratory dynamics of the subject P. The horizontal axis represents the time axis, and the vertical axis represent the amplitude of the respiration. A rise in the waveform represents an inspiratory dynamic, and a drop in the waveform represents an expiratory dynamic.

For example, in the CT respiratory waveform illustrated in FIG. 4, it is assumed that time T1 is the time at which the CT scan is executed (from the start time to the end time), the time being recorded in a manner associated with the CT respiratory waveform. Under such an assumption, the reconstructing function 734 identifies that the CT respiratory phase during the execution of the CT scan is an expiratory phase, based on the position of the time T1 in the CT respiratory waveform. The reconstructing function 734 then identifies a respiration period P2 and a respiration period P3 in the PET respiratory phase corresponding to the CT respiratory phase, from the PET respiratory waveform illustrated in FIG. 5. The reconstructing function 734 then extracts the raw PET data corresponding to the respiration periods P2, P3 acquired by the PET scan, from the raw PET data acquired by the PET scan from which the PET respiratory waveform is acquired, as the gating data.

The respiratory phase in the gating data extracted in the process described above results in the same respiratory phase for which the CT image has been acquired. As a result, the PET image generated in the process at following Step S43 will be a PET image having the attenuation corrected, with the effect of the respiratory movement suppressed. Therefore, the reconstructing function 734 can improve the image quality of a PET image by using a CT image in the attenuation correction.

The way in which the respiratory phase is identified is not limited to the example described above. For example, the reconstructing function 734 may also identify the respiratory phase based on one of the start time and end time of the CT scan. As one example, when the time required in the CT scan is known in advance, one of the start time and the end time can be derived from the other. Therefore, when the time required in the CT scan is known in advance, the reconstructing function 734 can identify the respiratory phase during the time in which the CT scan is executed, based on one of the start time and the end time thereof.

Furthermore, in such a case, the respiratory waveform acquiring function 732 may be configured to record one of the start time and the end time of the CT scan.

The reconstructing function 734 may also identify the respiratory phase based on the depth and the amount of change in the respiration. For example, when the time at which the CT scan is executed is the time T1, the reconstructing function 734 identifies the depth (amplitude) of the respiration at the time T1, and the amount of change in the direction in which the amplitude increases or decreases, as the respiratory phase. The reconstructing function 734 then identifies time T2 and time T3 at which the PET respiratory phase having the identified depth and amount of change of the respiratory phase appears, from the PET respiratory waveform illustrated in FIG. 5. The reconstructing function 734 then establishes, using the time T2 and the time T3 as references, given respiration periods (e.g., P2 and P3), respectively, by extending the time in both directions from the references. The reconstructing function 734 then extracts the gating data acquired by the PET scan executed in the established respiration periods.

In this manner, the reconstructing function 734 can reconstruct a PET image by using an attenuation-correcting CT image, and gating data acquired under the same respiration conditions including the depth and the amount of change at the time of the CT image scan. Therefore, the reconstructing function 734 can generate a PET image having a high image quality with the attenuation corrected and the effect of the respiratory movement suppressed, in the same manner as in the example described above.

Figure 6:
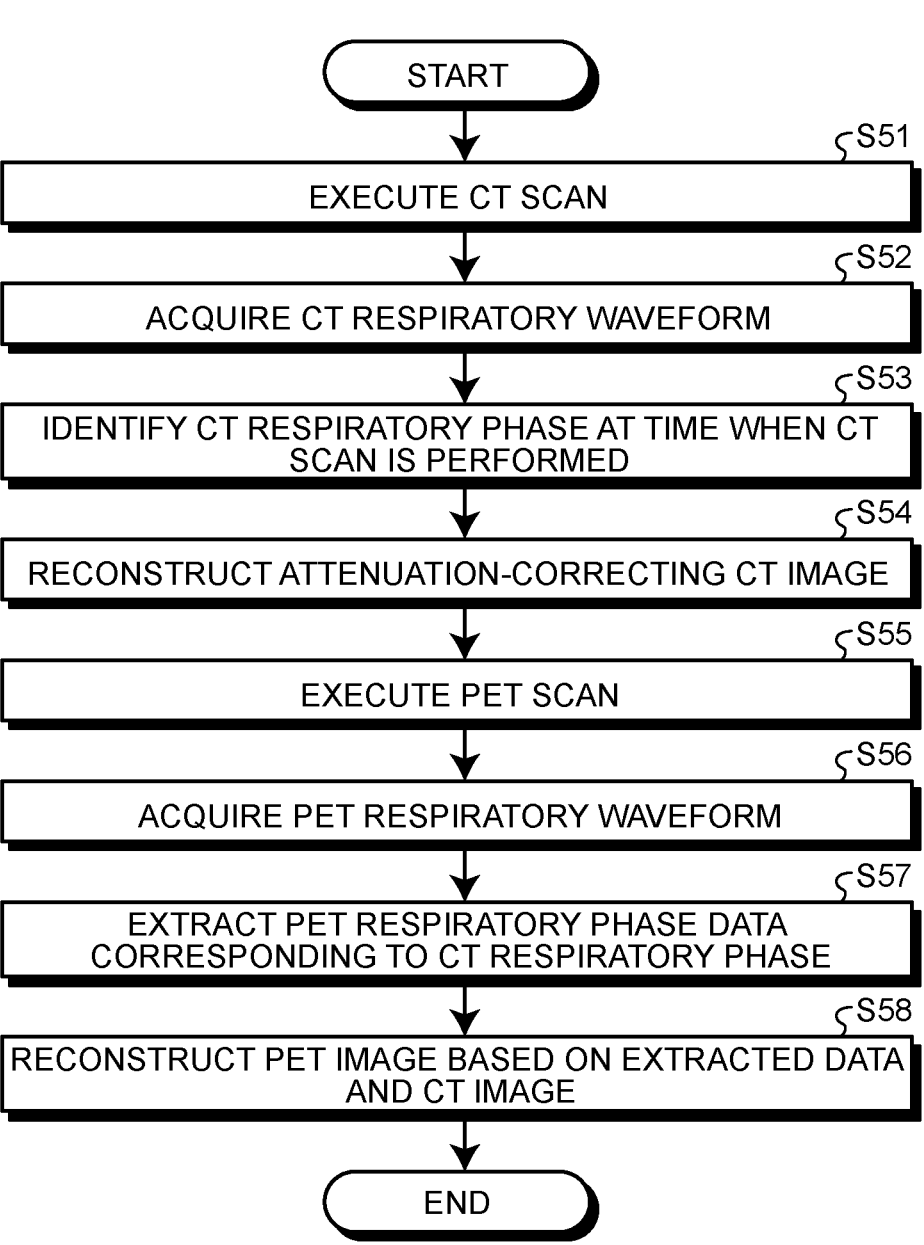
FIG. 6 is a flowchart illustrating one example of a scanning process performed by processing circuitry in the PET-CT apparatus according to the embodiment.

One example of the scanning process performed by the processing circuitry 73 in the PET-CT apparatus 1 will now be explained with reference to FIG. 6. FIG. 6 is a flowchart illustrating one example of the scanning process performed by the processing circuitry 73 in the PET-CT apparatus 1. In this process, a scanning process in which the attenuation-correcting CT image is acquired first and then the PET image is reconstructed using the CT image will be explained.

To begin with, the image capturing control function 733 execute a CT scan for acquiring an attenuation-correcting CT image, by controlling the CT gantry 30 (Step S51). The respiratory waveform acquiring function 732 then acquires a CT respiratory waveform from the monitoring data acquired by the infrared camera 60, by cooperating with the monitor control function 731 (Step S52). The reconstructing function 734 also identifies the CT respiratory phase at the time when the CT scan is performed, from the CT respiratory waveform, based on the time at which the CT scan is executed (Step S53).

When the CT scan is finished, the reconstructing function 734 also reconstructs the attenuation-correcting CT image based on the CT raw data acquired by the CT scan (Step S54).

The image capturing control function 733 executes a PET scan by controlling the PET gantry (Step S55). The respiratory waveform acquiring function 732 then acquires a PET respiratory waveform from the monitoring data acquired by the infrared camera 60, by cooperating with the monitor control function 731 (Step S56).

The image capturing control function 733 then extracts raw PET data acquired during a period of a PET respiratory phase corresponding to the CT respiratory phase, based on the CT respiratory phase identified at Step S53 and the PET respiratory waveform, and generates gate data (Step S57).

The image capturing control function 733 then reconstructs the PET image based on the extracted gate data and the attenuation-correcting CT image (Step S58), and ends the process.

The PET-CT apparatus 1 described above acquires an attenuation-correcting CT image by scanning the subject P, and identifies the CT respiratory phase of the subject P at the time of the CT image scan. The PET-CT apparatus 1 also acquires PET scan data based on the gamma rays emitted from the subject P, and generates gate data by gating the PET scan data based on the CT respiratory phase. The PET-CT apparatus 1 then reconstructs a PET image based on the attenuation-correcting CT image and the gate data.

Based on the above, with the PET-CT apparatus 1 according to the embodiment, it is possible to reconstruct a PET image applied with attenuation correction using an attenuation-correcting CT image and gating data acquired under the same condition of the respiratory phase as that of the time of the CT image scan. In other words, with the PET-CT apparatus 1, because it is possible to improve the precision in the synchronization of the respiratory phase between the CT image and the raw PET data at the time of reconstructing a PET image, it is possible to generate a PET image having the attenuation corrected, with the effect of respiratory movement suppressed. Hence, with the PET-CT apparatus 1, it is possible to improve the image quality of a PET image by using a CT image in attenuation correction.

The embodiment described above may be implemented in a manner modified as appropriate, by changing the functions or some of the functions included in the PET-CT apparatus 1. Therefore, some modifications of the embodiment described above will now be explained as other embodiments. In the explanation below, differences with respect to the embodiment described above will be mainly explained, and detailed explanations of the matters that are the same as those having already described above will be omitted. The modifications to be explained below may be implemented separately, or in an appropriate combination.

First Modification

Explained in the above embodiment is a configuration in which the infrared camera 60 is used as a monitoring apparatus that monitors the respiration of the subject P. However, the monitoring apparatus is not limited to the infrared camera 60. For example, the monitoring apparatus may be an image capturing apparatus capturing images in a frequency band other than the infrared.

As one example, the monitoring apparatus may be a terahertz camera capturing images in a terahertz band. The terahertz camera detects the energy of electromagnetic waves in the terahertz band, emitted from an object. When a terahertz camera is used as the monitoring apparatus, the monitoring apparatus outputs monitoring data representing the terahertz-band energy emitted from a human body (the body temperature is the heat source), and the terahertz-band energy emitted from objects other than a human body, as temperature differences.

In such a case, the respiratory waveform acquiring function 732 acquires the respiratory waveform of the subject P from the monitoring data output from the terahertz camera, based on a change in the image in the area along the boundary between the body region and the other region (temperature change), or a temperature change in the portion corresponding to the human body, in the same manner as in the embodiment described above.

By using the terahertz camera, it is possible to derive a respiratory waveform from the data output from the terahertz camera installed in a dark place, or even when a drape of the like is placed on the subject P, for example, in the same manner as with the infrared camera.

As another example, the monitoring apparatus may be an optical camera such as a digital camera capturing images in the visible spectrum. When an optical camera is used as the monitoring apparatus, a marker is put on the abdomen of the subject P, for example, and the optical camera captures the body region having the marker installed.

In such a case, the respiratory waveform acquiring function 732 detects the movements of the marker (the movement in accordance with the respiration of the subject P) represented in the monitoring data output from the optical camera, and acquires the respiratory waveform of the subject P, based on the detected marker movement.

In the manner described above, even when a monitoring apparatus other than the infrared camera 60 is used, it is possible to acquire the respiratory waveform of the subject P contactlessly, in the same manner as in the embodiment described above. Therefore, the PET-CT apparatus 1 according to this modification can achieve the same advantageous effects achieved by the embodiment described above.

Second Modification

Explained in the above embodiment is an implementation in which the respiratory waveform of the subject P is acquired from the monitoring data output from the monitoring apparatus (the infrared camera 60), but it is also possible to acquire information other than the respiratory waveform.

For example, monitoring data records bodily movements of the subject P moving his/her body, as well as the respiratory dynamics of the subject P. Such a bodily movement during a scan becomes a cause of an artifact, so that it is preferable to exclude the data at the time of bodily movements from the data used in reconstruction.

Therefore, for example, the respiratory waveform acquiring function 732 detects a bodily movement other than the respiration of the subject P from the monitoring data, and records the time at which the bodily movement has occurred, in a manner associated with the respiratory waveform. Specifically, the respiratory waveform acquiring function 732 records the time at which the bodily movement has occurred, in a manner associated with the PET respiratory waveform at the time of the PET scan. The reconstructing function 734 then excludes the time in which the bodily movement has occurred, from the PET respiratory waveform, and identifies the respiration period corresponding to the CT phase. The reconstructing function 734 then extracts the raw PET data acquired at the time of the respiration, and generates the gate data. The reconstructing function 734 according to this modification corresponds to a second identifying unit.

In this manner, the PET-CT apparatus 1 according to this modification can execute reconstruction by excluding the raw PET data at the time when the bodily movement of the subject P has occurred. Therefore, the PET-CT apparatus 1 according to this modification can acquire a PET image having a higher image quality, by suppressing the artifact caused by bodily movements.

Furthermore, when the infrared camera 60 is used as the monitoring apparatus, information indicating the body temperature of the subject P is also recorded in the monitoring data from the monitoring apparatus. There are some clinical applications in the body temperature of the subject P, e.g., in determining the condition of the subject P.

Therefore, for example, the processing circuitry 73 in the respiratory waveform acquiring function 732 or the like may also acquire body temperature information indicating the body temperature of the subject P from the monitoring data of the infrared camera 60. Furthermore, the processing circuitry 73 may also store the information of the body temperature of the subject P acquired from the monitoring data together with a PET image, or output such information on the display 74, for example.

In this manner, with the PET-CT apparatus 1, it is possible to clinically make a secondary use of the body temperature information of the subject P, acquired at the time of the scan. The destination to which the body temperature information is output is not limited to the display 74. For example, the processing circuitry 73 may output the information of the body temperature of the subject P to an external apparatus or system such as RIS, together with the subject ID or the like identifying the subject P.

Explained in the above embodiment is an example in which the functional configurations of the PET-CT apparatus 1 are implemented by the processing circuitry 73, but the embodiment is not limited thereto. For example, the functional configurations explained herein may also be implemented using hardware only, or a combination of hardware and software may be used to implement the same functions.

The term "processor" used in the above explanation means circuitry such as a CPU, an MPU, an GPU, an ASIC, or a programmable-logic device (such as an SPLD, a CPLD, and an FPGA). The processor implements a function by reading a computer program stored in the memory 75, and executing the computer program. Instead of storing the computer program in the memory 75, it is also possible to incorporate the computer program directly into the processor circuitry. In such a case, the processor implements a function by reading a computer program incorporated in the circuitry, and executing the computer program. Furthermore, the processor according to the embodiment is not limited to a configuration including a single piece of circuitry, but may also be configured as one processor including a combination of a plurality of independent pieces of circuitry to implement the functions.

The computer program executed by the processor is provided in a manner incorporated in the ROM or memory circuitry in advance. This computer program may also be provided in a manner recorded in a computer-readable storage medium such as a compact disc read-only memory (CD-ROM), a flexible disk (FD), a compact disc recordable (CD-R), or a digital versatile disc (DVD), as a file in a format installable to such an apparatus or as a file in an executable format. Furthermore, this computer program may be stored in a computer connected to a network such as the Internet, and made available for download or distributed over the network. For example, this computer program has a modular configuration including the functional units described above. As the actual hardware, by causing the CPU to read the computer program from a storage medium such as the ROM and executing the computer program, each of these modules is loaded onto the main memory, and generated on the main memory.

According to at least one of the embodiment and the like described above, it is possible to improve the image quality of a PET image by using a CT image in attenuation correction.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A PET-CT apparatus, comprising:
a CT scanner configured to scan a subject to acquire CT scan data;
a PET scanner configured to detect a gamma ray emitted from the subject to acquire PET scan data; and
processing circuitry configured to:
  acquire camera data obtained by a camera configured to scan the subject while the CT scanner scans the subject and configured to scan the subject while the PET scanner detects the gamma ray;
  generate correction data for attenuation correction based on the CT scan data;
  identify, based on the camera data, a respiratory phase of the subject corresponding to the CT scan data that is used for generating the correction data;
  exclude a first period from the PET scan data based on the camera data, the first period being a period during which a movement of the subject that is different from a respiration of the subject occurs while the PET scanner detects the gamma ray;
  identify a second period in the PET scan data from which the first period has been excluded, the second period corresponding to the identified respiratory phase; and
  reconstruct a PET image based on the generated correction data and a part of the PET scan data corresponding to the second period.

2. The PET-CT apparatus according to claim 1, wherein the processing circuitry is further configured to:
acquire a respiratory waveform from the camera data in which respiratory dynamics of the subject are recorded; and
identify the respiratory phase based on the respiratory waveform.

3. The PET-CT apparatus according to claim 1, wherein the camera is an infrared camera that visualizes infrared emitted from the subject.

4. The PET-CT apparatus according to claim 1, wherein the camera is a terahertz camera that visualizes a terahertz-band electromagnetic wave emitted from the subject.

5. The PET-CT apparatus according to claim 1, wherein the camera is an optical camera that captures an image of a marker placed on a body of the subject.

6. The PET-CT apparatus according to claim 1, wherein a part of the CT scan data corresponding to another respiratory phase different from the respiratory phase identified based on the camera data is not used for the generation of the correction data.

7. A medical image processing method, comprising:
scanning a subject with a CT scanner to acquire CT scan data;
detecting, by a PET scanner, a gamma ray emitted from the subject to acquire PET scan data;
acquiring camera data obtained by a camera configured to scan the subject while the CT scanner scans the subject and configured to scan the subject while the PET scanner detects the gamma ray;

generating correction data for attenuation correction based on the CT scan data;

identifying, based on the camera data, a respiratory phase of the subject corresponding to the CT scan data that is used for generating the correction data;

excluding a first period from the PET scan data based on the camera data, the first period being a period during which a movement of the subject that is different from a respiration of the subject occurs while the PET scanner detects the gamma ray;

identifying a second period in the PET scan data from which the first period has been excluded, the second period corresponding to the identified respiratory phase;

and reconstructing a PET image based on the generated correction data and a part of the PET scan data corresponding to the second period.

\* \* \* \* \*